(12) United States Patent
Ishikawa

(10) Patent No.: US 10,583,751 B2
(45) Date of Patent: Mar. 10, 2020

(54) EYE POINT MEASURING DEVICE AND EYE POINT MEASURING METHOD

(71) Applicant: TOYOTA BOSHOKU KABUSHIKI KAISHA, Aichi-ken (JP)

(72) Inventor: Takuya Ishikawa, Aichi-ken (JP)

(73) Assignee: TOYOTA BOSHOKU KABUSHIKI KAISHA, Aichi-ken (JP)

( * ) Notice: Subject to any disclaimer, the term of this patent is extended or adjusted under 35 U.S.C. 154(b) by 84 days.

(21) Appl. No.: 15/848,709

(22) Filed: Dec. 20, 2017

(65) Prior Publication Data

US 2018/0178678 A1  Jun. 28, 2018

(30) Foreign Application Priority Data

Dec. 27, 2016  (JP) ................................ 2016-252819

(51) Int. Cl.
*B60N 2/02* (2006.01)
*G06F 3/01* (2006.01)
*A61B 3/113* (2006.01)
*G06T 7/73* (2017.01)
*G02B 27/01* (2006.01)

(52) U.S. Cl.
CPC ........... *B60N 2/02* (2013.01); *G02B 27/0172* (2013.01); *G02B 27/0179* (2013.01); *G06F 3/013* (2013.01); *A61B 3/113* (2013.01); *B60N 2002/0272* (2013.01); *G02B 2027/0138* (2013.01); *G06T 7/73* (2017.01); *G06T 2207/10012* (2013.01)

(58) Field of Classification Search
CPC .. B60N 2/02; G02B 27/0172; G02B 27/0179; G06F 3/013; A61B 3/113
See application file for complete search history.

(56) References Cited

U.S. PATENT DOCUMENTS

| | | | | |
|---|---|---|---|---|
| 2008/0089559 | A1* | 4/2008 | Koumura | A61B 3/113 382/117 |
| 2012/0069301 | A1* | 3/2012 | Hirata | A61B 3/112 351/209 |
| 2012/0154441 | A1* | 6/2012 | Kim | G06K 9/00832 345/633 |

(Continued)

FOREIGN PATENT DOCUMENTS

JP   2015-206764   11/2015

*Primary Examiner* — Santiago Garcia
(74) *Attorney, Agent, or Firm* — Greenblum & Bernstein, P.L.C.

(57) ABSTRACT

An eye point measuring device configured to measure a three-dimensional position of an eye of an occupant sitting on a seat device of a vehicle by using a monocular camera positioned at a fixed position, wherein the eye point measuring device calculates the three-dimensional position of the eye of the occupant based on: a position change amount between a position of the eye of the occupant before the adjustment of the position of the seat device and a position of the eye of the occupant after the adjustment of the position of the seat device in a superimposed image in which an initial image and an after-adjustment image are superimposed on each other; a component, parallel to the superimposed image, of a movement amount of the seat device from a position before the adjustment to a position after the adjustment; and an angle of view of the monocular camera.

5 Claims, 3 Drawing Sheets

(56) References Cited

U.S. PATENT DOCUMENTS

| | | | | |
|---|---|---|---|---|
| 2013/0096820 A1* | 4/2013 | Agnew | ................... | B60R 1/00 |
| | | | | 701/428 |
| 2015/0239398 A1* | 8/2015 | Kaplan | ................. | B60R 1/006 |
| | | | | 701/49 |
| 2016/0018889 A1* | 1/2016 | Skogo | ............... | H04N 5/23219 |
| | | | | 348/78 |
| 2016/0147297 A1* | 5/2016 | Rose | ...................... | G06F 3/013 |
| | | | | 345/156 |
| 2016/0170487 A1* | 6/2016 | Saisho | .............. | G01C 21/3635 |
| 2016/0196098 A1* | 7/2016 | Roth | ..................... | B60K 35/00 |
| | | | | 715/761 |
| 2016/0313562 A1* | 10/2016 | Saisho | .............. | G02B 27/0179 |
| 2017/0155867 A1* | 6/2017 | Yokota | .................. | B60K 35/00 |
| 2018/0197030 A1* | 7/2018 | Yamataka | ............... | G08G 1/16 |

\* cited by examiner

EYE POINT MEASURING DEVICE AND EYE POINT MEASURING METHOD

CROSS-REFERENCE TO RELATED APPLICATIONS

This application claims priority from Japanese Patent Application No. 2016-252819 filed on Dec. 27, 2016, the entire contents of which are incorporated herein by reference.

TECHNICAL FIELD

The disclosure relates to an eye point measuring device and eye point measuring method for measuring a three-dimensional position of an eye of an occupant sitting on a seat device of a vehicle by using a monocular camera positioned at a fixed position.

BACKGROUND

JP-A-2015-206764 discloses a technology for measuring a position of an eye of an occupant by using a monocular camera. The technology disclosed in JP-A-2015-206764 relates to a head-up display (HUD) device, and is configured such that the position of the eye of the occupant sitting on a seat device of a vehicle can be measured, and a display position of a display can be adjusted based on the position of the eye of the occupant. In the HUD device disclosed in JP-A-2015-206764, a depth distance (a distance from the monocular camera to a photographic object) of an image in which a face of the occupant is photographed is estimated based on a space dimension between left and right eyes of the occupant photographed by the monocular camera. That is, the depth distance of the image is estimated based on the fact that the space dimension between the left and right eyes increases as the occupant gets closer to the monocular camera, and the space dimension between the left and right eyes decreases as the occupant gets away from the monocular camera. Then, the position of the eye of the occupant is obtained by the depth distance and the image in which the face of the occupant is photographed.

In the above-described method for measuring the position of the eye of the occupant, the depth distance of the image is estimated based on the space dimension between the left and right eyes of the occupant photographed by the monocular camera. However, there are individual differences in space dimension between left and right eyes of the occupant, and it is difficult to accurately obtain the depth distance of the image according to the space dimension between left and right eyes. Therefore, there is a problem that measurement accuracy of the position of the eye of the occupant is low. Here, for example, it is possible to accurately measure the depth distance of the image by using a stereo camera, or the like. However, since two cameras are required, the cost increases.

SUMMARY

The disclosure provides an eye point measuring device and an eye point measuring method by which a position of an eye of an occupant at a low cost by a monocular camera can be measured accurately.

According to an aspect of the disclosure, there is provided an eye point measuring device configured to measure a three-dimensional position of an eye of an occupant sitting on a seat device of a vehicle by using a monocular camera positioned at a fixed position, the eye point measuring device including: the monocular camera; an image memory configured to store: data relating to an initial image of the eye of the occupant which was photographed by the monocular camera in a state where the occupant was sitting on the seat device before adjustment of a position of the seat device; and data relating to an after-adjustment image of the eye of the occupant which was photographed by the monocular camera in a state where the occupant was sitting on the seat device after the adjustment of the position of the seat device; and a controller configured to calculate the three-dimensional position of the eye of the occupant based on: a position change amount between a position of the eye of the occupant before the adjustment of the position of the seat device and a position of the eye of the occupant after the adjustment of the position of the seat device in a superimposed image in which the initial image and the after-adjustment image are superimposed on each other; a component, parallel to the superimposed image, of a movement amount of the seat device from a position before the adjustment to a position after the adjustment; and an angle of view of the monocular camera.

According to another aspect of the disclosure, there it provided an eye point measuring method which measures a three-dimensional position of an eye of an occupant sitting on a seat device of a vehicle by using a monocular camera positioned at a fixed position, the eye point measuring method including: obtaining an initial image by photographing the eye of the occupant by the monocular camera in a state where the occupant is sitting on the seat device; obtaining an after-adjustment image by photographing the eye of the occupant by the monocular camera in a state where the occupant is sitting on the seat device after adjustment of a position of the seat device; and calculating the three-dimensional position of the eye of the occupant based on: a position change amount between a position of the eye of the occupant before the adjustment of the position of the seat device and a position of the eye of the occupant after the adjustment of the position of the seat device in a superimposed image in which the initial image and the after-adjustment image are superimposed on each other; a component, parallel to the superimposed image, of a movement amount of the seat device from a position before the adjustment to a position after the adjustment; and an angle of view of the monocular camera.

According to the disclosure, a position of an eye of an occupant can be accurately measured at a low cost by a monocular camera.

DETAILED DESCRIPTION

First Embodiment

Hereinafter, an eye point measuring device 20 according to a first embodiment of the disclosure will be described with reference to FIGS. 1 to 5. The eye point measuring device 20 according to the first embodiment is a device which measures a position of an eye of an occupant M sitting on a seat device 12 of a driver seat of a passenger vehicle 10. A front-rear direction, a left-right direction and an upper-lower direction shown in figures correspond to a front-rear direction, a left-right direction and an upper-lower direction of the passenger vehicle 10.

<Summary of the Seat Device 12 of the Passenger Vehicle 10>

Figure 1:
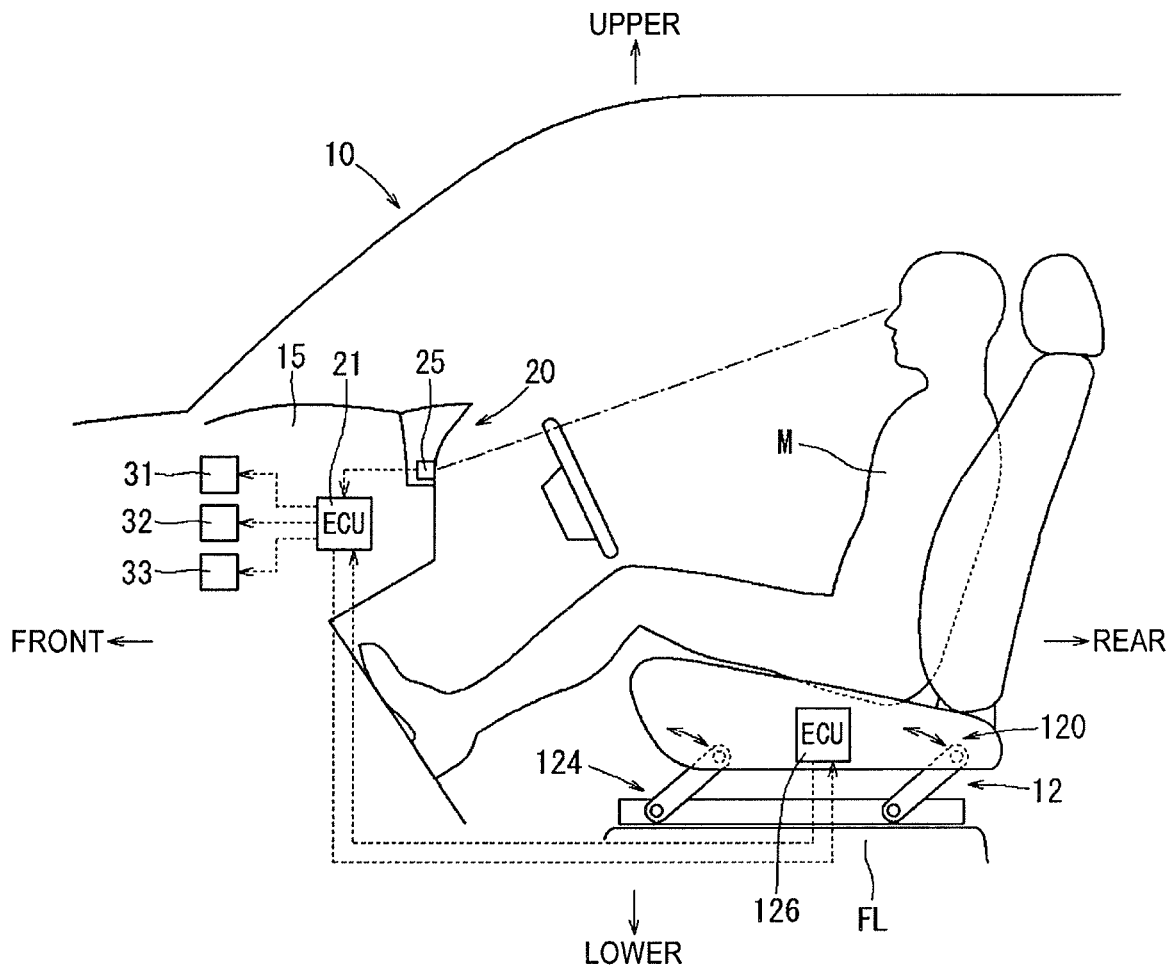
FIG. 1 is an overall schematic view showing a configuration of an eye point measuring device according to a first embodiment of the disclosure.

The summary of the seat device 12 of the driver seat of the passenger vehicle 10 will be described before the eye point measuring device 20 is described. As shown in FIG. 1, the seat device 12 includes a seat main body portion 120, a slide lifting/lowering mechanism 124 configured to slide the seat main body portion 120 forward or rearward and lift and lower the seat main body portion 120 with respect to a vehicle cabin floor FL, a seat ECU 126 configured to control the slide lifting/lowering mechanism 124, or the like. The seat ECU 126 is configured to operate the slide lifting/lowering mechanism 124 or the like based on a signal from an operation switch (not shown), or the like, so as to adjust a front-rear position, a height position, or the like of the seat main body portion 120. Further, data relating to a forward sliding amount and a lifting amount from an original position (a rear end position and a lower end position) of the seat main body portion 120 is transmitted from the seat ECU 126 to a vehicle ECU 21.

<Configuration of the Eye Point Measuring Device 20>

As shown in FIG. 1, the eye point measuring device 20 includes a monocular camera 25 and the vehicle ECU 21. The vehicle ECU 21 is configured to be able to calculate a three-dimensional position of the eye of the occupant M based on image data of the monocular camera 25, a movement amount of the seat main body portion 120 of the seat device 12, or the like. The monocular camera 25 is fixed at a predetermined position on a surface of an instrument panel 15 of the passenger vehicle 10 in a state of facing a direction of a face of the occupant sitting on the seat main body portion 120 of the seat device 12.

Figure 2:
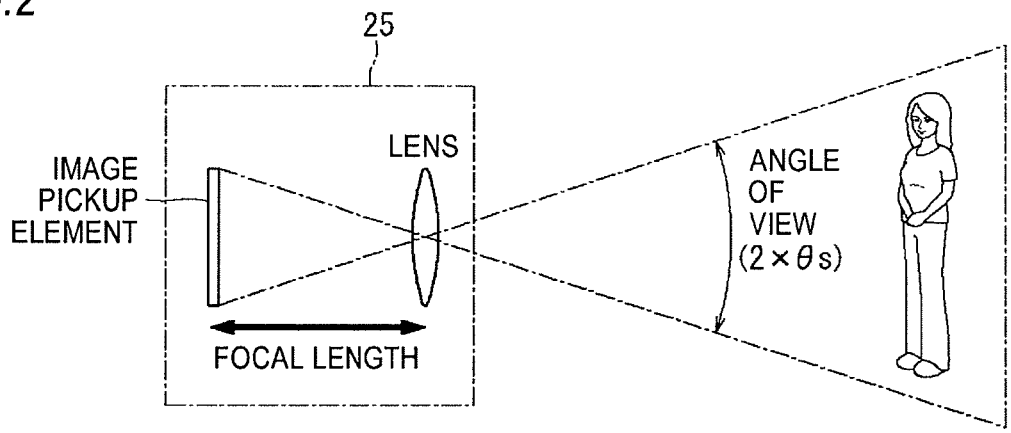
FIG. 2 is a schematic view showing an angle of view of a monocular camera of the eye point measuring device.
Figure 3:
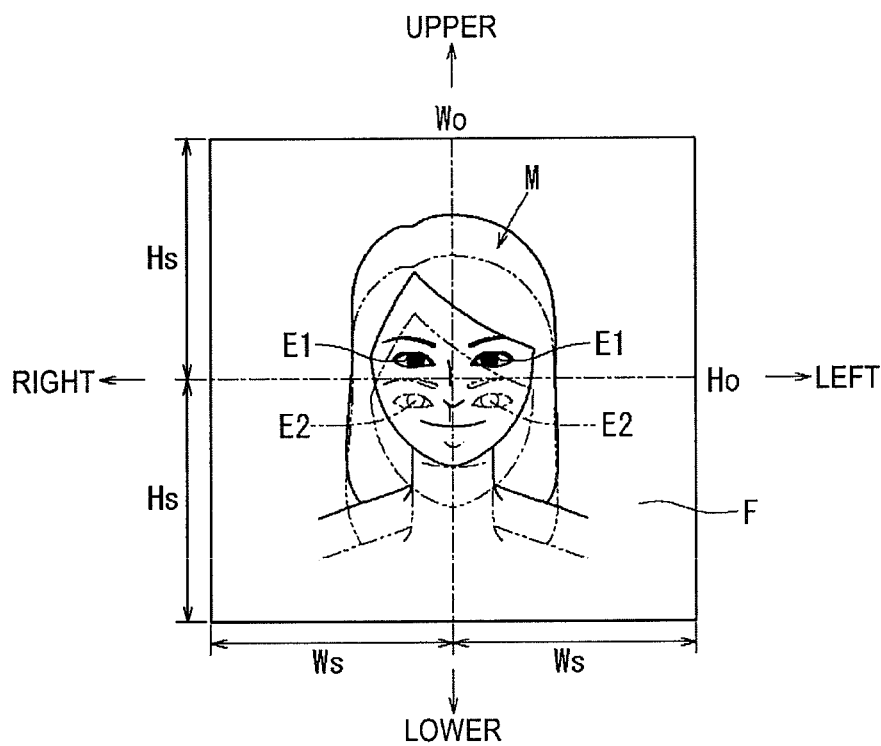
FIG. 3 is a diagram showing an example of an image of the monocular camera.

As shown in FIG. 2, in the monocular camera 25, an angle of view determining a range of a photographic object captured in a photographed image F (static image) is set to a constant value, for example, 2×θs. That is, both a horizontal angle of view and a vertical angle of view of the monocular camera 25 are set to 2×θs. Therefore, since the horizontal angle of view and the vertical angle of view are set to an equal value, as shown in FIG. 3, the image F of the monocular camera 25 is formed into a square (Ws=Hs). Herein, as shown in FIG. 2, a size of an actual photographic object (actual image) can be represented by multiplying a size of a virtual image captured in an image pickup element of the monocular camera 25 by a predetermined magnification. Therefore, for the convenience of explanation, the size of the actual photographic object is used as the size of image F of the monocular camera 25 in the following description.

Figure 4:
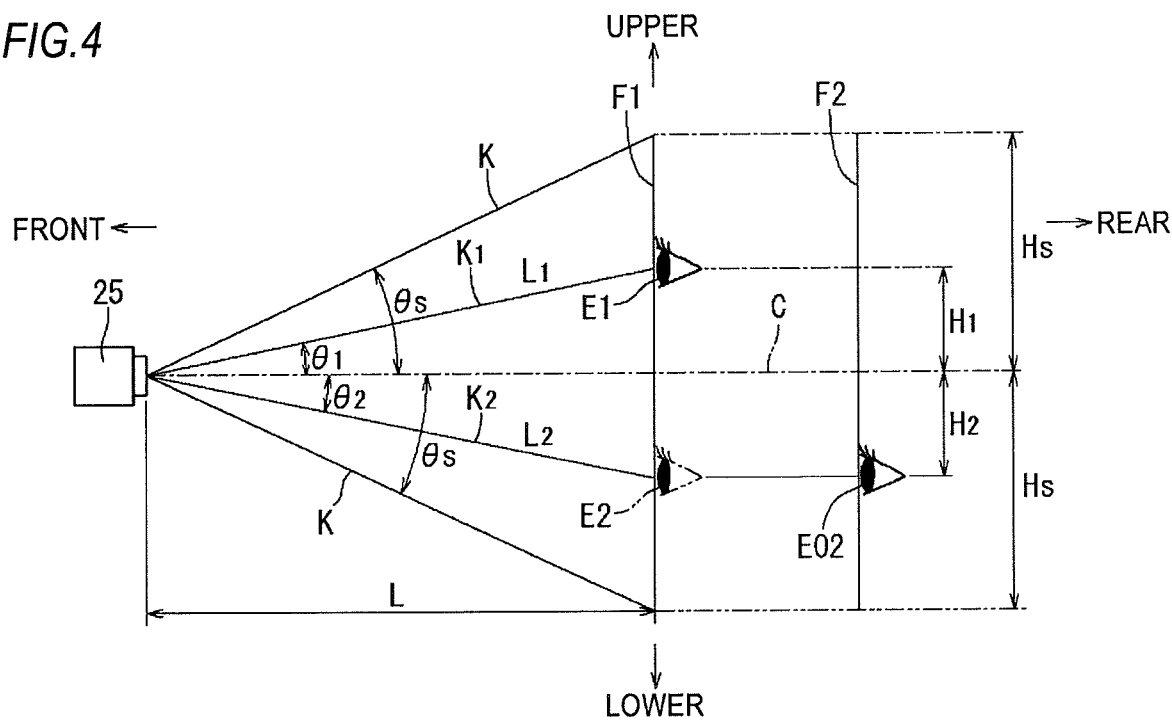
FIG. 4 is a side view showing a relationship between the monocular camera and a photographic object (image)

That is, in FIGS. 3 and 4, a distance Hs from a center of the image F to an upper end or a lower end of the image F represents a distance from a position corresponding to the center of the image F to a position corresponding to the upper end or the lower end of the image F in the actual photographic object. Similarly, a distance Ws (Ws=Hs) from the center of the image F to a left end or a right end of the image F represents a distance from a position corresponding to the center of the image F to a position corresponding to the left end or right end of the image F in the actual photographic object (refer to FIG. 3). Further, as shown in FIG. 4, an angle $\theta s$ which is formed by a straight line C (hereinafter, referred to as a central line C) passing through a lens center (center) of the monocular camera 25 and the center of the image F, and a straight line K passing through the center of the monocular camera 25 and an upper end center or a lower end center of the image F is a half of the vertical angle of view (2×θs) of the monocular camera 25. Similarly, an angle $\theta s$ which is formed by the central line C, and a straight line passing through the center of the monocular camera 25 and a left end center or a right end center of the image F is a half of the horizontal angle of view (2×θs).

Therefore, a distance L (a depth distance L of the image F) from a position of the monocular camera 25 to a position of the photographic object which is equivalent to the center of the image F is represented by the following Equation 1 (L=Hs/tan θs) from FIG. 4. Herein, as shown in FIG. 3, the monocular camera 25 is positioned such that the center of the image F is substantially aligned with a center of the face of the occupant sitting on the seat device 12 (the seat main body portion 120).

<Eye Point Measuring Method>

Figure 5:
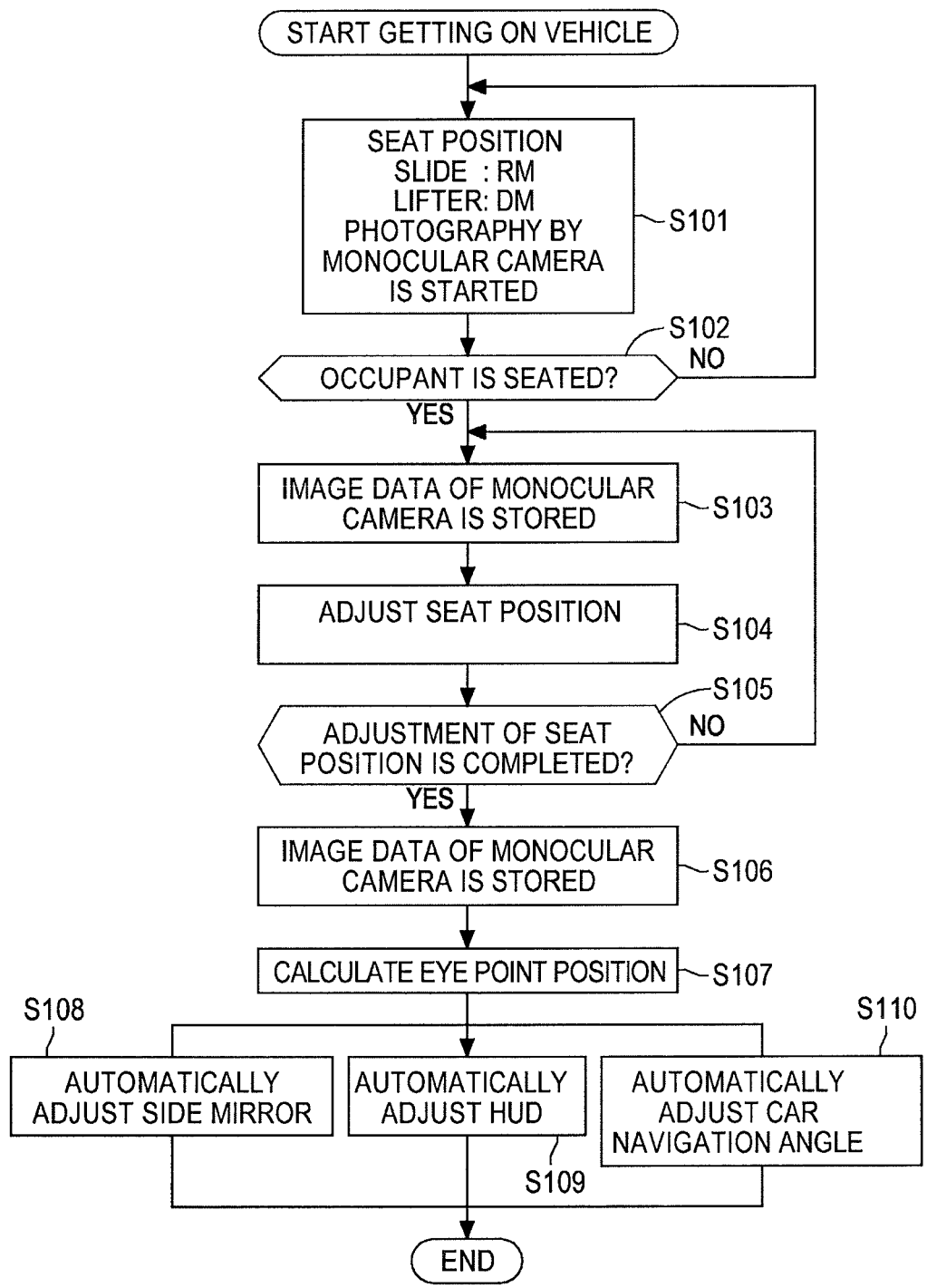
FIG. 5 is a flowchart showing operations of the eye point measuring device.

Next, an eye point measuring method will be described based on a flowchart shown in FIG. 5. Herein, the flowchart is executed based on a program stored in a memory of the vehicle ECU 21. First, when the occupant starts getting on the vehicle, the seat main body portion 120 is returned to an original position, that is, the rear end position and the lower end position by operating the slide lifting/lowering mechanism 124 of the seat device 12 (step S101). Therefore, a large space is secured in front of the seat main body portion 120, and the occupant can easily get on the vehicle. Furthermore, photography by the monocular camera 25 is started when the occupant starts getting on the vehicle (step S101).

When the occupant sitting on the seat apparatus 12 (seat main body portion 120) is detected (YES in step S102), for example, by a seating sensor or the like, the image data (an initial image F2) of the monocular camera 25 after the occupant took a seat is stored (step S103). Then, the occupant operates the slide lifting/lowering mechanism 124 to adjust a seat position of the seat main body portion 120 (step S104). Therefore, the seat main body portion 120 slides forward and rises, and the occupant also moves forward and upward with the movement of the seat main body portion 120. Then, when the adjustment of the seat position is completed (YES in step S105), the image data (the after-adjustment image F1) of the monocular camera 25 is stored at this timing again (step S106). Next, in step S107, the calculation (eye point position calculation) for obtaining the three-dimensional position of the eye of the occupant is executed.

As shown in FIGS. 3 and 4, the eye point position calculation is performed using the initial image F2 and the after-adjustment image F1. As described above, position adjustment of the seat device 12 is performed by sliding the seat main body portion 120 forward and further lifting the seat main body portion 120 from the original position. Therefore, as shown in FIGS. 3 and 4, a position E1 of the eye of the occupant in the after-adjustment image F1 moves forward and upward with respect to a position E02 of the eye of the occupant in the initial image F2.

In the eye point position calculation, as shown in FIGS. 3 and 4, the after-adjustment image F1 and the initial image F2 are superimposed with the centers thereof being aligned. Accordingly, the position E1 of the eye of the occupant after adjustment and a position E2 of the eye of the occupant before the adjustment are shown in the after-adjustment image F1. Then, on the after-adjustment image F1, a distance H2 in a height direction from a center C of the image F to the position E2 of the eye of the occupant before the adjustment, and a distance H1 in the height direction from the center C of the image F to the position E1 of the eye of the occupant after the adjustment are calculated. Here, since the position E2 of the eye of the occupant before the adjustment and the position E1 of the eye of the occupant after the adjustment are positioned above and below the center C of the image F, (H1+H2) is the movement amount of the occupant in an upward direction.

In a case where the position E2 of the eye of the occupant before the adjustment and the position E1 of the eye of the occupant after the adjustment are both above or both below the center C of the image F, a difference between the distance H1 and the distance H2 is the movement amount of the occupant in the upward direction. The movement amount of the occupant in the upward direction is equal to the movement amount of the seat main body portion 120 of the seat device 12 in the upward direction. The movement amount of the seat main body portion 120 in the upward direction is calculated based on data of the seat ECU 126.

As shown in FIG. 4, a line segment connecting the position E1 of the eye of the occupant after the adjustment in the after-adjustment image F1 and the center of the monocular camera 25 is denoted as a line segment K1, and an angle between the line segment K1 and the central line C is denoted as $\theta 1$. Further, a distance between the position E1 of the eye of the occupant after the adjustment and the center of the monocular camera 25 is denoted as L1. A line segment connecting the position E2 of the eye of the occupant before the adjustment in the after-adjustment image F1 and the center of the monocular camera 25 is denoted as a line segment K2, and an angle between the line segment K2 and the central line C is denoted as $\theta 2$. Furthermore, a distance between the position E2 of the eye of the occupant before the adjustment and the center of the monocular camera 25 is denoted as L2.

In this state, the law of cosines is applied in a triangle composed of the line segment K1, the line segment K2, and a line segment connecting positions E1 and E2 of the eye of the occupant. Accordingly, Equation 2 of $(H1+H2)^2=(L1)^2+(L2)^2-2\times L1\times L2\times \cos(\theta 1+\theta 2)$ is obtained. Herein, a depth distance L of the image F is represented by Equation 3 of $L=L1\cos\theta 1$ or Equation 4 of $L=L2\cos\theta 2$.

Therefore, when Equation 3 and Equation 4 are substituted into Equation 2 and are rearranged, the depth distance L of the image F is represented by formula 1.

[Formula 1]

$$L = \frac{H1 + H2}{\sqrt{\frac{1}{\cos^2 \theta 1} + \frac{1}{\cos^2 \theta 2} - \frac{2 \cos(\theta 1 + \theta 2)}{\cos \theta 1 \cdot \cos \theta 2}}} \quad \text{Equation 5}$$

$\theta 1$ in Equation 5 is represented by Equation 6 of $\theta 1=\tan^{-1}(H1/L)$ according to FIG. 4. Besides, L is represented by Equation 1 of $L=Hs/\tan\theta s$. Thus, by substituting Equation 1 into Equation 6, $\theta 1$ is represented by Equation 7 of $\theta 1=\tan^{-1}((H1/Hs)\times \tan\theta s)$.

$\theta 2$ in Equation 5 is represented by Equation 8 of $\theta 2=\tan^{-1}(H2/L)$. Thus, by substituting Equation 1 into Equation 8, $\theta 2$ is represented by Equation 9 of $\theta 2=\tan^{-1}((H2/Hs)\times \tan\theta s)$.

As described above, (H1+H2) is the movement amount of the seat main body portion 120 in the upward direction.

Therefore, the depth distance L of the image F is calculated by the angle of view ($2\theta s$) of the monocular camera, the distance Hs from a center of the image F1 to an upper end or a lower end of the image F1, and (H1+H2) which is the movement amount of the seat main body portion 120 in the upward direction. In this manner, it is possible to obtain the position E1 of the eye of the occupant with respect to the center of the monocular camera 25 by obtaining the depth distance L of the image F.

When the position E1 of the eye of the occupant is obtained, data relating to the position E1 of the eye of the occupant is transmitted to an automatic side mirror adjustment device 31, an automatic head-up display adjustment device 32, and an automatic car navigation adjustment device 33 to adjust an angle of a monitor, or the like so as to correspond to the position E1 of the eye of the occupant (steps S107, S108, and S109). The above-described memory of the vehicle ECU 21 is equivalent to an image memory according to the disclosure, and a CPU of the vehicle ECU 21 is equivalent to the controller according to the disclosure.

Advantages of the Eye Point Measuring Device 20 According to the First Embodiment According to the disclosure, the vehicle ECU 21 (controller) is configured to calculate the three-dimensional position of the eye of the occupant based on: a position change amount (H1+H2) between a position of the eye of the occupant before the adjustment of the position of the seat device and a position of the eye of the occupant after the adjustment of the position of the seat device in a superimposed image in which the initial image and the after-adjustment image are superimposed on each other; a component (H1+H2), parallel to the superimposed image, of a movement amount of the seat device from a position before the adjustment to a position after the adjustment; and an angle of view ($2\times\theta s$) of the monocular camera. That is, the three-dimensional position of the eye of the occupant can be accurately obtained by replacing the position change amount between the positions of the eye of the occupant before and after position adjustment of the seat device 12 with the component, parallel to the image, of the movement amount of the seat device 12. Therefore, by using data relating to the movement amount of the seat device 12, the three-dimensional position of the eye of the occupant can be accurately measured by the monocular camera. For hits reason, compared with a method for measuring a three-dimensional position of the eye of the occupant using a stereo camera, a distance sensor, or the like, cost reduction can be achieved.

In addition, the seat device 12 is configured to be slid forward and rearward and lifted and lowered, and in the superimposed image, the position change amount between the position of the eye of the occupant before the adjustment of the position of the seat device and the position of the eye of the occupant after the adjustment of the position of the seat device is a position change amount in a vertical direction. In other words, a horizontal position of the eye of the occupant before the adjustment of the position of the seat device and a horizontal position of the eye of the occupant after the adjustment of the position of the seat device are the same. Therefore, it is unnecessary to consider a movement of the eye of the occupant in the horizontal direction, and the calculation for obtaining the position of the eye of the occupant is simplified. Further, by outputting the data relating to the position of the eye of the occupant to an automatic side mirror adjustment device 31 by the vehicle ECU 21 (controller), side mirror can be adjusted based on the position of the eye of the occupant. Similarly, the automatic head-up display (HUD) adjustment device 32, the automatic car navigation adjustment device 33, or the like can be operated based on the position of the eye of the occupant.

Modifications

The disclosure is not limited to the above-described embodiment, and modifications can be made without departing from the spirit and scope of the disclosure. For example, in the eye point measuring device 20 according to the first embodiment, an example of measuring the position of the eye of the occupant sitting on the seat device 12 which is able to be slid forward and rearward and lifted and lowered is shown. However, it is also possible to measure the position of the eye of the occupant sitting on the seat device 12 which slides rotary. In addition, in the first embodiment, an example in which the monocular camera 25 is fixed at the instrument panel 15 of the passenger vehicle is shown. However, it is also possible to fix the monocular camera 25 to a ceiling portion of the vehicle cabin or a position of a room mirror. Further, in the first embodiment, an example in which both the horizontal angle of view and the vertical angle of view of the monocular camera 25 are set to an equal value (2×θs) is shown. However, it is also possible to set the horizontal angle of view and the vertical angle of view of the monocular camera 25 to different values. Furthermore, in the first embodiment, an example in which the position of the eye of the occupant sitting on the seat device 12 of the driver seat is shown. However, it is also possible to measure the position of the eye of the occupant which is sitting on a seat device other than the driver seat.

What is claimed is:

1. An eye point measuring device configured to measure a three-dimensional position of an eye of an occupant sitting on a seat device of a vehicle by using a monocular camera positioned at a fixed position, the eye point measuring device comprising: the monocular camera; an image memory configured to store:
    data relating to an initial image of the eye of the occupant which was photographed by the monocular camera in a state where the occupant was sitting on the seat device before adjustment of a position of the seat device; and
    data relating to an after-adjustment image of the eye of the occupant which was photographed by the monocular camera in a state where the occupant was sitting on the seat device after the adjustment of the position of the seat device; and
a controller configured to calculate the three-dimensional position of the eye of the occupant based on:
a position change amount between a position of the eye of the occupant before the adjustment of the position of the seat device and a position of the eye of the occupant after the adjustment of the position of the seat device in a superimposed image in which the initial image and the after-adjustment image are superimposed on each other;
a component, parallel to the superimposed image, of a movement amount of the seat device from a position before the adjustment to a position after the adjustment; and
an angle view of the monocular camera, wherein the controller is configured to replace the position change amount between the position of the eye of the occupant before the adjustment of the position of the seat device and the position of the eye of the occupant after the adjustment of the position of the seat device with the component parallel to the superimposed image to calculate the three-dimensional position of the eye.

2. The eye point measuring device according to claim 1, wherein the seat device is configured to be slid forward and rearward and lifted and lowered, and
wherein, in the superimposed image, the position change amount between the position of the eye of the occupant before the adjustment of the position of the seat device and the position of the eye of the occupant after the adjustment of the position of the seat device is a position change amount in a vertical direction.

3. The eye point measuring device according to claim 1, wherein the seat device is configured to be slid forward and rearward and lifted and lowered, and
wherein, in the superimposed image, a horizontal position of the eye of the occupant before the adjustment of the position of the seat device and a horizontal position of the eye of the occupant after the adjustment of the position of the seat device are the same.

4. The eye point measuring device according to claim 1, wherein the controller is further configured to output data relating to the calculated three-dimensional position of the eye of the occupant.

5. An eye point measuring method which measures a three-dimensional position of an eye of an occupant sitting on a seat device of a vehicle by using a monocular camera positioned at a fixed position, the eye point measuring method comprising:
    obtaining an initial image by photographing the eye of the occupant by the monocular camera in a state where the occupant is sitting on the seat device;
    obtaining an after-adjustment image by photographing the eye of the occupant by the monocular camera in a state where the occupant is sitting on the seat device after adjustment of a position of the seat device; and
    calculating, with a controller, the three-dimensional position of the eye of the occupant based on:
a position change amount between a position of the eye of the occupant before the adjustment of the position of the seat device and a position of the eye of the occupant after the adjustment of the position of the seat device in a superimposed image in which the initial image and the after-adjustment image are superimposed on each other;
a component, parallel to the superimposed image, of a movement amount of the seat device from a position before the adjustment to a position after the adjustment; and
an angle of view of the monocular camera, wherein
the controller is configured to replace the position change amount between the position of the eye of the occupant before the adjustment of the position of the seat device and the position of the eye of the occupant after the adjustment of the position of the seat device with the component parallel to the superimposed image to calculate the three-dimensional position of the eye.

* * * * *